United States Patent [19]

Rotter

[11] Patent Number: 4,520,807

[45] Date of Patent: Jun. 4, 1985

[54] OBSTETRIC DEVICE AND METHOD

[76] Inventor: Carl W. Rotter, 6461 Brookedge Ct., Dublin, Ohio 43017

[21] Appl. No.: 487,999

[22] Filed: Apr. 29, 1983

Related U.S. Application Data

[63] Continuation of Ser. No. 275,857, Jun. 22, 1981, abandoned.

[51] Int. Cl.³ .............................................. A61F 5/46
[52] U.S. Cl. ............................................... 128/132 D
[58] Field of Search ......................... 128/132 D, 132 R

[56] References Cited

U.S. PATENT DOCUMENTS

| 1,711,924 | 4/1929 | Weitzner | 137/454.2 |
| 3,364,928 | 1/1968 | Creager, Jr. et al. | 128/132 D |
| 3,452,750 | 7/1969 | Blanford | 128/283 |

*Primary Examiner*—John D. Yasko
*Assistant Examiner*—Christa K. Scott
*Attorney, Agent, or Firm*—Yount & Tarolli

[57] ABSTRACT

Apparatus for minimizing and most likely eliminating contamination during an obstetrical delivery and repair, said apparatus comprising a shield having a drape portion and having an adhesive carrying surface zone above the drape portion, the shield being disposed to be positioned with the drape portion locatable over the anus, and with the adhesive carrying surface zone adjacent to and in facing relation with the perineum and the perineal area, having at least a portion of the zone being locatable between the vagina and the anal openings, and pressing the adhesive carrying surface zone of the shield into tight engagement with the perineum and perineal area for restricting flow with the drape portion of fecal material from the anus into the operative area during obstetrical delivery and repair when this is needed.

2 Claims, 3 Drawing Figures

OBSTETRIC DEVICE AND METHOD

This application is a continuation of application Ser. No. 275,857, filed June 22, 1981, now abandoned.

BACKGROUND AND SUMMARY OF THE INVENTION

This invention relates to an apparatus and a method for minimizing, and most likely eliminating, contamination during an obstetrical delivery and repair.

In the pre-operative treatment of the obstetric patient in the labor room, it is sometimes customary to clean out the lower intestinal tract with an enema to evacuate most of the solid stool from the lower colon and rectum, hopefully to reduce contamination by stool at the time of delivery.

However, whether or not an enema is given, there is still considerable risk of contamination during delivery and repair. This is because the enema is generally not sufficient to provide for expulsion of all fecal material from the bowel. Hence, during delivery and repair great care is necessary to minimize the risk of contamination. Means to prevent expulsion of intestinal fluids and solids into the sterile, local site during delivery and subsequent repair is highly desirable.

One form of prior art device which has been suggested to avoid contamination is shown in U.S. Pat. No. 1,711,294 granted April 30, 1929 to G. Weitzner on an "Obstetric Device". This device comprises a flexible tube closed at one end, having a relatively rigid rim or ring surrounding the opening thereof and having a flexible sheet 10 surrounding the opening. Sheet 10 is provided with a skin adherent pressure sensitive adhesive 11 on the side which is to contact the perineum. This is a rectal closure device which is designed to hold back the intestinal contents before they are expelled through the use of a pouch or bag 14 for collecting fecal material and which is extruded from the rectum by the pressure of matter collecting therein. The device is not believed capable of solving the problem of contamination because the device will become detached and expelled during the severe pressures which occur during child birth. Further, the device may also become detached by the pressure of the collected fecal material. In addition, in the applicant's experience, the medical profession has been quite leery of devices which require insertion into the rectum.

The apparatus of the present invention is designed to greatly minimize contamination by directing fecal material from the rectal cavity away from the sterile, obstetric, operative site during delivery and repair. The apparatus is simple to apply, and yet is believed to effectively prevent contamination with fecal material even under the extreme pressures which often occur during child birth. Moreover, the apparatus of the invention achieves those objectives without being inserted into the rectum.

The apparatus of the invention preferably comprises a shield having a drape portion and an adhesive carrying surface zone above the drape portion. The shield is disposed to be positioned with drape portion locatable over the anus, and with the adhesive carrying surface zone adjacent to and in facing relation with the perineum and the perineal area. Moreover, at least a portion of the adhesive carrying surface zone is locatable between the vagina and the anal opening. In applying the apparatus, the adhesive carrying surface zone is pressed into tight engagement with the perineum and perineal area and the drape portion is positioned so as to guide or channel fecal material away from the sterile obsteric site during obstetrical delivery and repair.

BRIEF DESCRIPTION OF THE DRAWINGS

The invention is illustrated in the accompanying drawings showing a preferred embodiment, including specific parts and arrangement of parts. It is intended that the drawings, included as a part of this specification, be only illustrative of a preferred embodiment of the invention and should in no way be considered as a limitation upon the invention itself.

DETAILED DESCRIPTION OF THE PREFERRED EMBODIMENT

As noted above, the present invention relates to an apparatus, method and/or procedure for greatly minimizing the risk of contamination, and most likely eliminating contamination, during an obstetrical delivery and repair.

As is well known, after her labor progresses to a certain point, the obstetrical patient is taken to the delivery room where her baby is then delivered. In the delivery room, the patient may be anesthetized and then placed in the lithotomy (or delivery) position. She is, at this time, preped by the delivery room nurse with a soap, water solution and appropriate antiseptic to thoroughly cleanse the entire area surrounding the delivery site to make that area as sterile as possible. It is this area where the sterility must be protected to the fullest extent possible throughout the entire delivery and repair procedure. In conventional delivery procedures, the obstetrician then dries the skin carefully and thoroughly after he or she is in sterile gown and gloves. He or she then applies shield 10 in place after first wiping the skin dry in the area where the adhesive portion of the shield will adhere to the skin. Just prior to this the obstetrician pulls off the protective paper covering the adhesive part of the shield. After this, the obstetrician drapes the patient and proceeds with the delivery. The present invention contemplates application of the shield, to be described hereinafter, just after the patient is covered and before the obstetrician proceeds with delivery.

Figure 1:
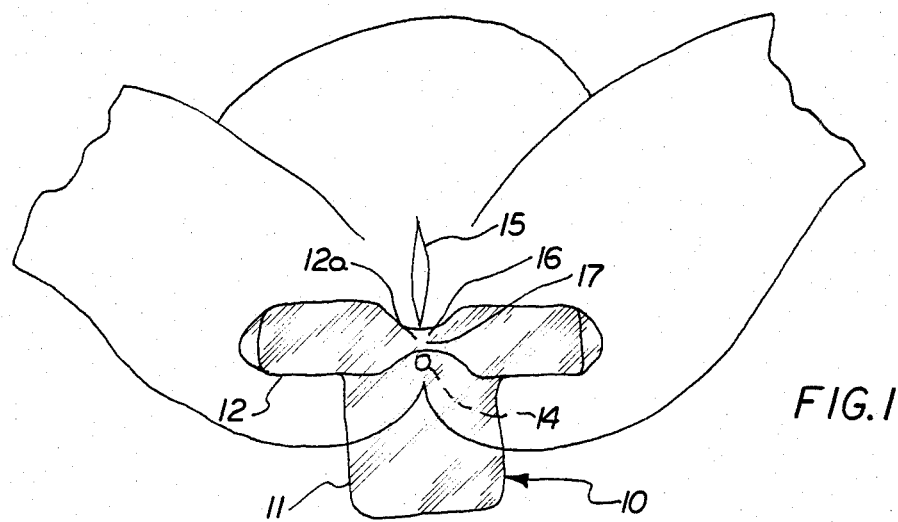
FIG. 1 is a bottom view of an obstetrical patient in the obstetrical delivery position and to which the apparatus of the present invention is adhered during delivery and repair.
Figure 2:
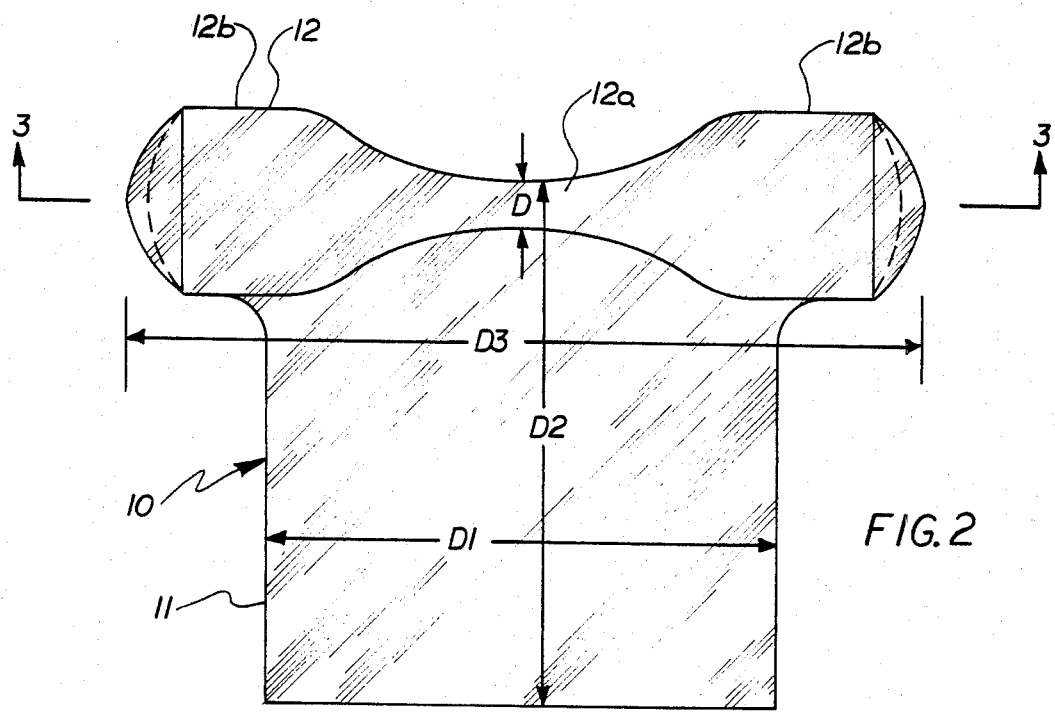
FIG. 2 is a front elevational view of the apparatus of the present invention in the form of a shield with a protective, peel-off strip still adhered to its adhesive carrying surface zone.

In FIGS. 1 and 2, the apparatus in accordance with the present invention is shown as shield 10, which makes an excellent barrier against fecal contamination. Shield 10 is preferably formed of a transparent, flexible, plastic material, such as polyvinylchloride or other suitable plastic, which is essentially impervious to fecal material. Shield 10 has a downwardly extending drape portion 11, and an adhesive carrying surface zone 12 above drape portion 11. The adhesive carrying surface zone 12 is a band extending along the top edge of shield 10, as shown by the solid lines at the top of FIG. 2. It has a narrower central portion 12a of adhesive, whose width dimension D is less than the distance between the anus 14 and vagina 15 of the obstetrical patient. The adhesive carrying surface zone 12 is bow-tie shaped, being narrow enough in its central portion 12a to fit between the anus 14 and vagina 15, and having adequate adhesive in its wider portions 12b to support shield 10.

Figure 3:
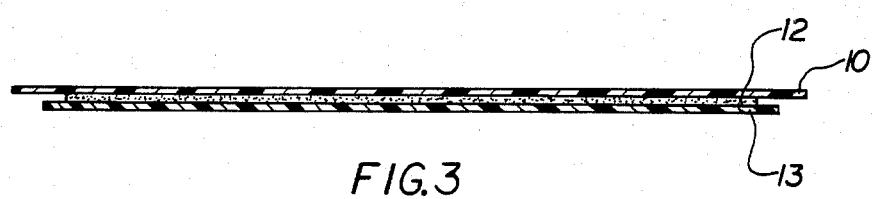
FIG. 3 is a horizontal, sectional view of the apparatus taken generally along the line 3—3 in FIG. 2.

The preferred embodiment contemplates that adhesive-carrying surface zone 12 and protective, peel off strip 13 can all be formed for shield 10 from a section of No. C707 Double Coated Cloth Tape sold by Arno Adhesive Tape, Inc., P.O. Box 301, Michigan City, Ind. 46360, a subsidiary of Scholl Co., Chicago, Ill. As seen in FIGS. 2 and 3, shield 10 can be formed by cutting the aforementioned tape into an appropriate shape and securing it to shield 10 above drape portion 11.

Shield 10 is intended to be applied to the obstetrical patient after the patient has been placed in the lithotomy (or delivery) position, after the patient is covered and before the obstetrician proceeds with delivery.

A method of using shield 10 comprises the steps of peeling back strip 13 off adhesive 12, locating the shield with the central portion 12a of the adhesive coated surface zone 12 disposed between the patient's anus and vagina and the drape portion 11 covering the anus, and pressing the adhesive coated surface zone 12 of shield 10 against perineum 16 and perineal area 17 between vagina 15 and anus 14. With the shield positioned in that manner, it prevents leakage of fecal material into the operative area in the region of vagina 15 because the adhesive coated surface zone 12 physically blocks or seals the area between the anus 14 and vagina 15, and the drape portion 11, which hangs down from adhesive coated surface zone 12, directs any leakage of fecal material downwardly and away from the operative area associated with vagina 15. The flexibility of shield 10 permits it to drape over, conform to and adhere to body contours in FIG. 1. The transparency of shield 10 permits the attending obstetrician to monitor actions under shield 10, such as the bodily function at the anus.

The relative dimensions and characteristics of shield 10 and adhesive zone 12 are important in obtaining a workable, useful and successful shield 10 for the purposes described herein. If the shield does not have adequate shape and proportions, it will not cover the body area properly and contamination may result. If the shield is too large it becomes too heavy and the adhesive will not properly secure the shield to the patient. A satisfactory shield 10 has been obtained by having approximately the following dimensions: (1) width D1 of drape portion 11 being approximately 17 cm, (2) the total dimension D2 of the height of drape portion 11 and the width of narrower central portion 12a being approximately 17 cm, and (3) length D3 of adhesive-carrying zone 12 being approximately 26.5 cm. As to adhesive-carrying zone 12, note that: (1) adhesive zone 12 has narrow central portion 12a, whose width dimension D is less than the distance between anus 14 and vagina 15 in FIG. 1, so that adhesion will be maximized while neither opening is obstructed; (2) adhesive 12 is longer than the width of draped portion 11 (compare dimensions D3 and D1) so that there will be adequate adhesion, which will not be limited by the desirable dimensions of the drape portion over anus 14; and (3) a larger adhesive zone 12 is combined with drape portion 11 of adequate size and shape but not applying an excessive weight to the adhesive.

The adhesive characteristics of adhesive-carrying surface zone 12 can be enhanced if the perineum 16 is first cleaned and dried before attaching adhesive carrying zone 12 and shield 10, since adhesive 12 does not adhere readily to a wet surface. Further, it has been found that the adhesion is enhanced if the adhesive on shield 10 is sprayed with ethylchloride before it is pressed against the perineum.

The invention may be embodied in other specific forms without departing from the spirit or essential characteristics thereof. The present embodiment is therefore to be considered in all respects as illustrative and not restrictive with the scope of the invention being indicated by the appended claims rather than by the foregoing description, and all changes which come within the meaning and range of equivalency of the claims are therefore intended to be embraced therein.

I claim:

1. Apparatus for minimizing and most likely eliminating contamination during an obstetrical delivery and repair on a patient, said apparatus comprising a shield consisting essentially of a drape portion which consists essentially of a single sheet of material, an adhesive carrying surface zone connected to said drape portion, and a removable backing strip adhered to said adhesive carrying surface zone, said adhesive carrying surface zone being shaped so as to be locatable between the vagina and the anal opening without covering either the vagina or the anal opening and being pressable into tight engagement with the perineum and perineal area for forming a physical barrier between the vagina and the anal opening, and the drape portion extending away from the adhesive carrying surface zone and being positioned over the anal opening when said adhesive carrying surface zone is adjacent to and in facing relation with the perineum and the perineal area and when the patient is positioned for obstetrical delivery, so that said adhesive carrying surface zone physically blocks flow of fecal material from the anal opening to the vagina while allowing flow of fecal material from the anal opening and said drape portion directs fecal material from the anal opening away from the operative area during obstetrical delivery and repair, said adhesive carrying zone being bow-tie shaped, being narrow enough in its central portion to fit between the anus and the vagina, and having adequate adhesive in its wider portions to support the shield, the adhesive carrying zone being longer than the width of said drape portion, and the width and length of said drape portion being equal to each other.

2. An apparatus, as set forth in claim 1, further comprising the following relative dimensions:

the length of said adhesive carrying zone being approximately 26.5 cm, the width of said drape portion being approximately 17 cm, and the height of said drape portion and the width of the narrower central portion being approximately 17 cm, said drape portion being made of transparent material.

* * * * *